US012617677B1

(12) United States Patent
Ellsworth

(10) Patent No.: US 12,617,677 B1
(45) Date of Patent: May 5, 2026

(54) PROCESS AND APPARATUS FOR PRODUCING RENEWABLE FUELS

(71) Applicant: THE BOEING COMPANY, Chicago, IL (US)

(72) Inventor: Joseph M. Ellsworth, St. Louis, MO (US)

(73) Assignee: THE BOEING COMPANY, Arlington, VA (US)

( * ) Notice: Subject to any disclaimer, the term of this patent is extended or adjusted under 35 U.S.C. 154(b) by 828 days.

(21) Appl. No.: 17/738,850

(22) Filed: May 6, 2022

Related U.S. Application Data

(60) Provisional application No. 63/186,064, filed on May 7, 2021.

(51) Int. Cl.
| | |
|---|---|
| *C01B 3/38* | (2006.01) |
| *C01B 3/382* | (2026.01) |
| *C07C 29/151* | (2006.01) |
| *C10J 3/72* | (2006.01) |

(52) U.S. Cl.
CPC ............ *C01B 3/382* (2013.01); *C07C 29/151* (2013.01); *C10J 3/721* (2013.01); *C01B 2203/0283* (2013.01); *C10J 2300/0903* (2013.01); *C10J 2300/0916* (2013.01); *C10J 2300/0959* (2013.01); *C10J 2300/0973* (2013.01); *C10J 2300/1618* (2013.01); *C10J 2300/1659* (2013.01); *C10J 2300/1838* (2013.01)

(58) Field of Classification Search
CPC ............ C01B 3/382; C01B 2203/0283; C07C 29/151; C10J 3/721; C10J 2300/0916; C10J 2300/1618; C10J 2300/1659
See application file for complete search history.

(56) References Cited

U.S. PATENT DOCUMENTS

| | | | |
|---|---|---|---|
| 9,434,615 | B2 | 9/2016 | Kukkonen et al. |
| 9,647,284 | B2 | 5/2017 | Berlowitz et al. |
| 9,663,416 | B2 | 5/2017 | Lilga et al. |
| 9,771,533 | B2 | 9/2017 | Lilga et al. |
| 9,932,531 | B2 | 4/2018 | Lilga et al. |
| 10,005,974 | B2 | 6/2018 | Lilga et al. |
| 2012/0108675 | A1 | 5/2012 | Knuuttila et al. |
| 2013/0247448 | A1* | 9/2013 | Ampulski ............... C10L 1/023 |
| | | | 422/187 |

FOREIGN PATENT DOCUMENTS

| | | | |
|---|---|---|---|
| WO | WO-2011004066 A2 * | 1/2011 | ............. A61K 47/06 |
| WO | 2016067032 A1 | 5/2016 | |
| WO | 2016067033 A1 | 5/2016 | |
| WO | 2019148207 A1 | 8/2019 | |
| WO | 2019148208 A1 | 8/2019 | |

* cited by examiner

*Primary Examiner* — Keling Zhang
(74) *Attorney, Agent, or Firm* — Moore IP Law

(57) ABSTRACT

Aspects of the present disclosure generally relate to processes and apparatus for producing fuels and fuel compositions. In an aspect, a process for converting a carbon-containing feedstock is provided. The process includes drying a carbon-containing feedstock comprising biomass to form a terpene stream and a dried carbon-containing material, and hydrotreating the terpene stream to form a first hydrocarbon stream. The process further includes gasifying the dried carbon-containing material to form syngas, converting the syngas to a second hydrocarbon stream, and introducing the first hydrocarbon stream and the second hydrocarbon stream to form a fuel composition.

16 Claims, 4 Drawing Sheets

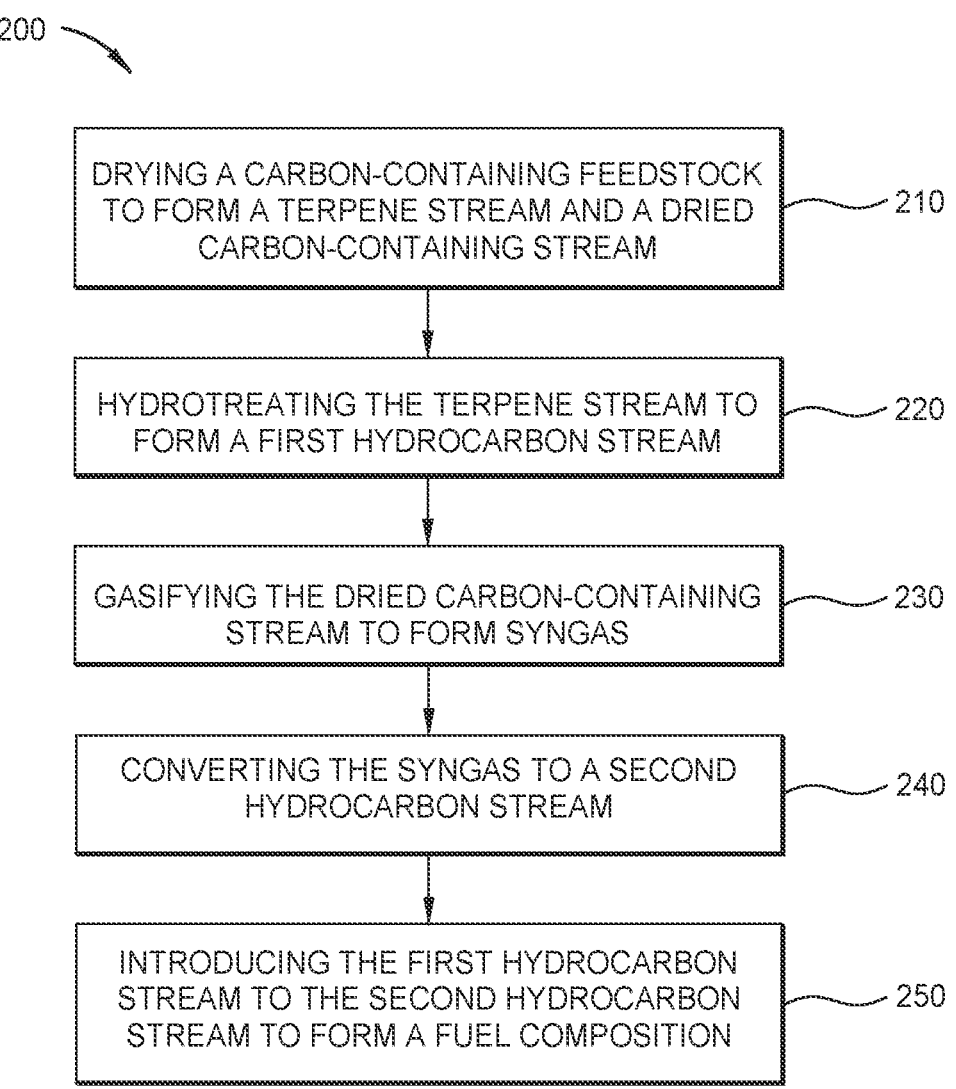

200

DRYING A CARBON-CONTAINING FEEDSTOCK TO FORM A TERPENE STREAM AND A DRIED CARBON-CONTAINING STREAM — 210

HYDROTREATING THE TERPENE STREAM TO FORM A FIRST HYDROCARBON STREAM — 220

GASIFYING THE DRIED CARBON-CONTAINING STREAM TO FORM SYNGAS — 230

CONVERTING THE SYNGAS TO A SECOND HYDROCARBON STREAM — 240

INTRODUCING THE FIRST HYDROCARBON STREAM TO THE SECOND HYDROCARBON STREAM TO FORM A FUEL COMPOSITION — 250

FIG. 2

PROCESS AND APPARATUS FOR PRODUCING RENEWABLE FUELS

CROSS-REFERENCE TO RELATED APPLICATION(S)

The present disclosure claims benefit of and priority to U.S. Provisional Patent Application Ser. No. 63/186,064 filed May 7, 2021, which is hereby incorporated by reference in its entirety.

FIELD

Aspects of the present disclosure generally relate to processes and apparatus for producing fuels and fuel compositions, and more specifically, to processes and apparatus for converting biomass into renewable fuels and compositions.

BACKGROUND

The development of sustainable and renewable sources of energy, including renewable fuels, to meet global energy demands is of great interest. Biomass, which is derived from, e.g., plant-based materials, is one such renewable energy source. As a source of carbon, biomass can be converted into a variety of valuable products and fuels useful for transportation such as jet fuel, diesel fuel, and gasoline. Conventional methods for converting biomass to fuels remain inefficient in terms of volumes produced from the biomass inputs.

There is a need for new and improved processes and apparatus for the production of fuels and fuel compositions from biomass.

SUMMARY

Aspects of the present disclosure generally relate to processes and apparatus for producing fuels and fuel compositions.

In an aspect, a process for converting a carbon-containing feedstock is provided. The process includes drying a carbon-containing feedstock comprising biomass to form a terpene stream and a dried carbon-containing material, and hydrotreating the terpene stream to form a first hydrocarbon stream. The process further includes gasifying the dried carbon-containing material to form syngas, converting the syngas to a second hydrocarbon stream, and introducing the first hydrocarbon stream and the second hydrocarbon stream to form a fuel composition.

In another aspect, a process for converting biomass is provided. The process includes converting biomass to a terpene stream and a dried carbon-containing material, and introducing the terpene stream with hydrogen and a hydrotreatment catalyst to form a first hydrocarbon stream. The process further includes introducing the dried carbon-containing material with a gasification agent to form syngas and converting at least a portion of the syngas to a second hydrocarbon stream. Converting at least a portion of the syngas to the second hydrocarbon stream includes introducing the syngas to a Fischer-Tropsch catalyst to form a second hydrocarbon stream, or introducing the syngas to a microorganism to form ethanol and oligomerizing ethanol to form a second hydrocarbon stream. The process further includes introducing the first hydrocarbon stream to the second hydrocarbon stream to form a fuel composition.

In another aspect, an apparatus for converting a carbon-containing feedstock is provided. The apparatus includes a drying unit coupled at a first end with a first end of a gasification unit, the drying unit further coupled at a second end with a first end of a hydrotreatment unit. The apparatus further includes a syngas conversion unit coupled at a first end with a second end of the gasification unit, and a collection unit coupled at a first end with a second end of the hydrotreatment unit, the collection unit further coupled at a second end with a second end of the syngas conversion unit.

BRIEF DESCRIPTION OF THE DRAWINGS

So that the manner in which the above recited features can be understood in detail, a more particular description, briefly summarized above, may be had by reference to example aspects, some of which are illustrated in the appended drawings.

FIG. 2 shows selected operations of an example process for converting a carbon-containing feedstock to a hydrocarbon product according to at least one aspect of the present disclosure.

DETAILED DESCRIPTION

Figure 1A:
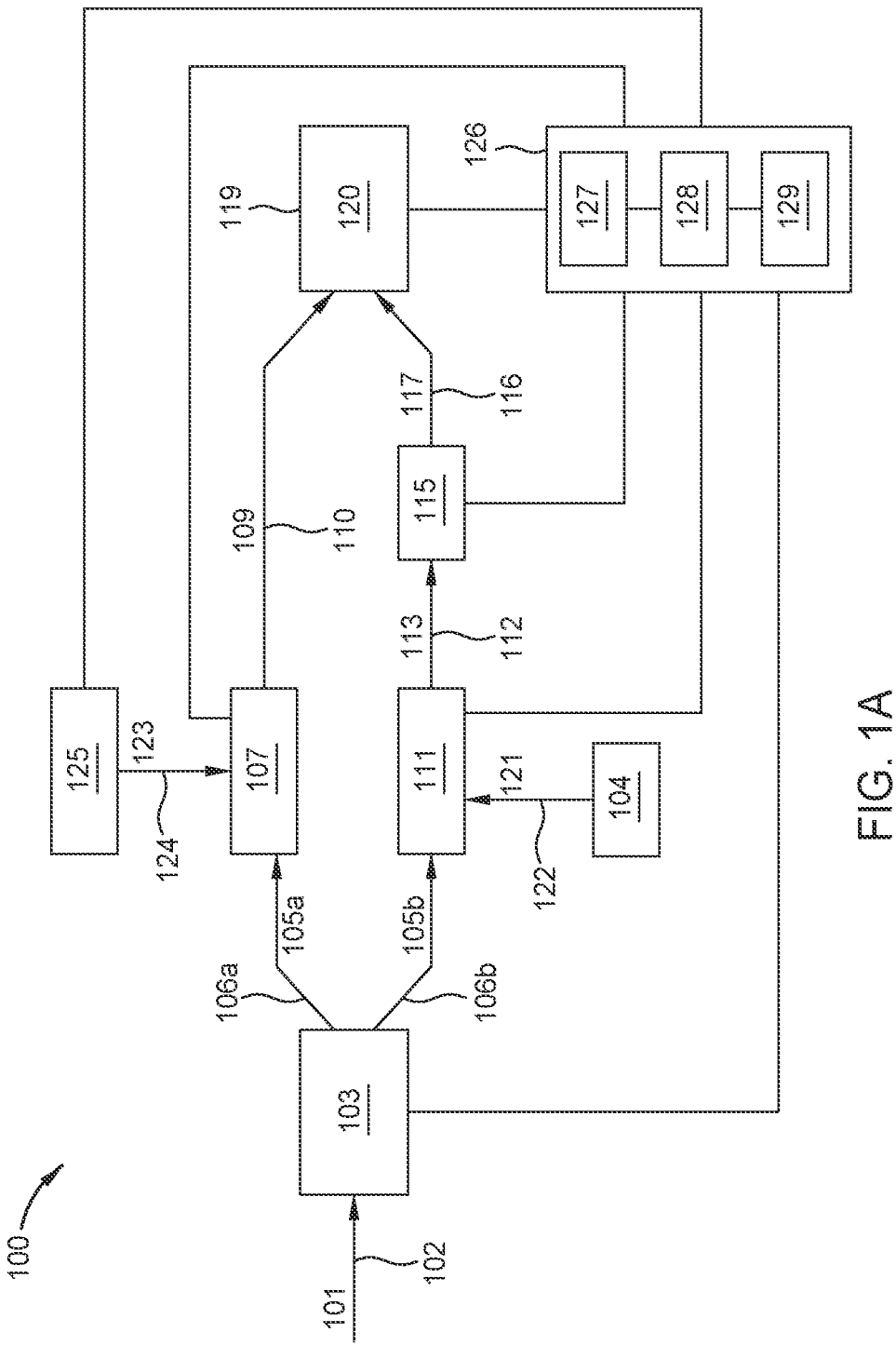
FIG. 1A is an example apparatus utilized for performing one or more operations of converting a carbon-containing feedstock to hydrocarbon products according to at least one aspect of the present disclosure.

Aspects of the present disclosure generally relate to processes and apparatus for producing fuels and fuel compositions. The inventor has found new and improved processes for manufacturing fuel compositions (or additives to be used in fuel compositions) from carbon-containing feedstocks such as biomass. Briefly, the process includes drying a carbon-containing feedstock to provide a terpene stream and a dried carbon-containing material. The terpene stream is converted to useful hydrocarbon products by hydrotreatment, while the dried carbon-containing material is converted to useful hydrocarbon products by a gasification reaction and subsequent Fischer-Tropsch reaction. Both streams of useful hydrocarbon products can then be combined to form a fuel composition. The fuel composition includes hydrocarbon components, e.g., diesel fuel, jet fuel, gasoline, and/or naphtha that can be used as fuels, additives for fuels, polymers, solvents, and other applications. As such, the hydrocarbon products made by processes herein are useful for, e.g., transportation applications such as land vehicles, aircraft, and watercraft.

The carbon-containing feedstock used as inputs for examples described herein can include, or be derived from, biomass. As such, processes described herein enable production of renewable fuels. Further, the fuels and fuel compositions described herein have increased energy density relative to conventional fuels and fuel compositions such as petroleum-derived fuels. The increased energy density is due to various streams/fuels produced according to aspects described herein—e.g., Fischer-Tropsch fuels and cycloalkyls-having no aromatic compounds. Aromatic compounds, which are components of petroleum derived fuels, contribute insignificantly to energy density and propulsive forces when combusted. Hence, the lack of aromatic compounds in streams/fuels described herein, enables the fuels to have higher relative amounts of molecules that contribute to energy density and propulsive forces when combusted. Cycloalkyl compounds, e.g., pinanes and derivatives thereof, have higher energy density than petroleum-derived fuels (linear and branched alkanes) due to, e.g., ring strain. For example, the resulting energy density increase for the fuel formulation can be from about 1% to about 40%. Upon combustion, these cycloalkyl compounds contribute to higher energy release than that of linear and branched alkanes. In some aspects, the fuels and fuel compositions include both Fischer-Tropsch fuels and cycloalkyl compounds.

Achieving an improved energy density by combining Fischer-Tropsch fuels and cycloalkyl compounds is not known. Moreover, and in contrast to conventional methods, the process described herein enable a single integrated process to make fuels and fuel compositions that include Fischer-Tropsch fuels and cycloalkyl compounds. Such a process has higher total efficiency in terms of the sum of chemical outputs relative to the chemical inputs. As a result, increased total volumes fuels and fuel compositions can be produced relative to conventional methods.

FIG. 1A is an apparatus 100 utilized for performing one or more operations of converting a carbon-containing feedstock 101 to hydrocarbon products, e.g., fuel compositions and/or additives for fuel compositions, according to at least one aspect of the present disclosure. The carbon-containing feedstock 101 can include biomass. Biomass refers to biological material that can be converted to a fuel. Illustrative, but non-limiting, examples of biomass include materials, by-products, and waste generated from, e.g., agricultural and forestry processes, such as agricultural matter and residues (e.g., wheat straw and corn), energy crops (e.g., wheatgrass and bamboo), forest residues (e.g., materials, by-products and waste from forest harvesting such as woodchips), plant- and algae-based matter and residues, and the like, and combinations thereof. In some aspects, biomass includes wood, leaves, pulps, stalks, grass material, shrubs, branches, energy crops, vegetables, fruits, flowers, grains, herbaceous crops, bark, needles, logs, trees, and combinations thereof. Additionally, or alternatively, biomass includes municipal solid waste, by-products and waste from wood-processing, by-products and waste from papermaking or timber processes, by-products and waste from agricultural and forestry activities, rotation crops, lumber, wood chips, sawdust, straw, firewood, wood materials, paper, waste paper, yard waste, and the like. Biomass can include any of the aforementioned materials, combinations of the aforementioned materials, in any proportion.

Figures 1B, 1C:
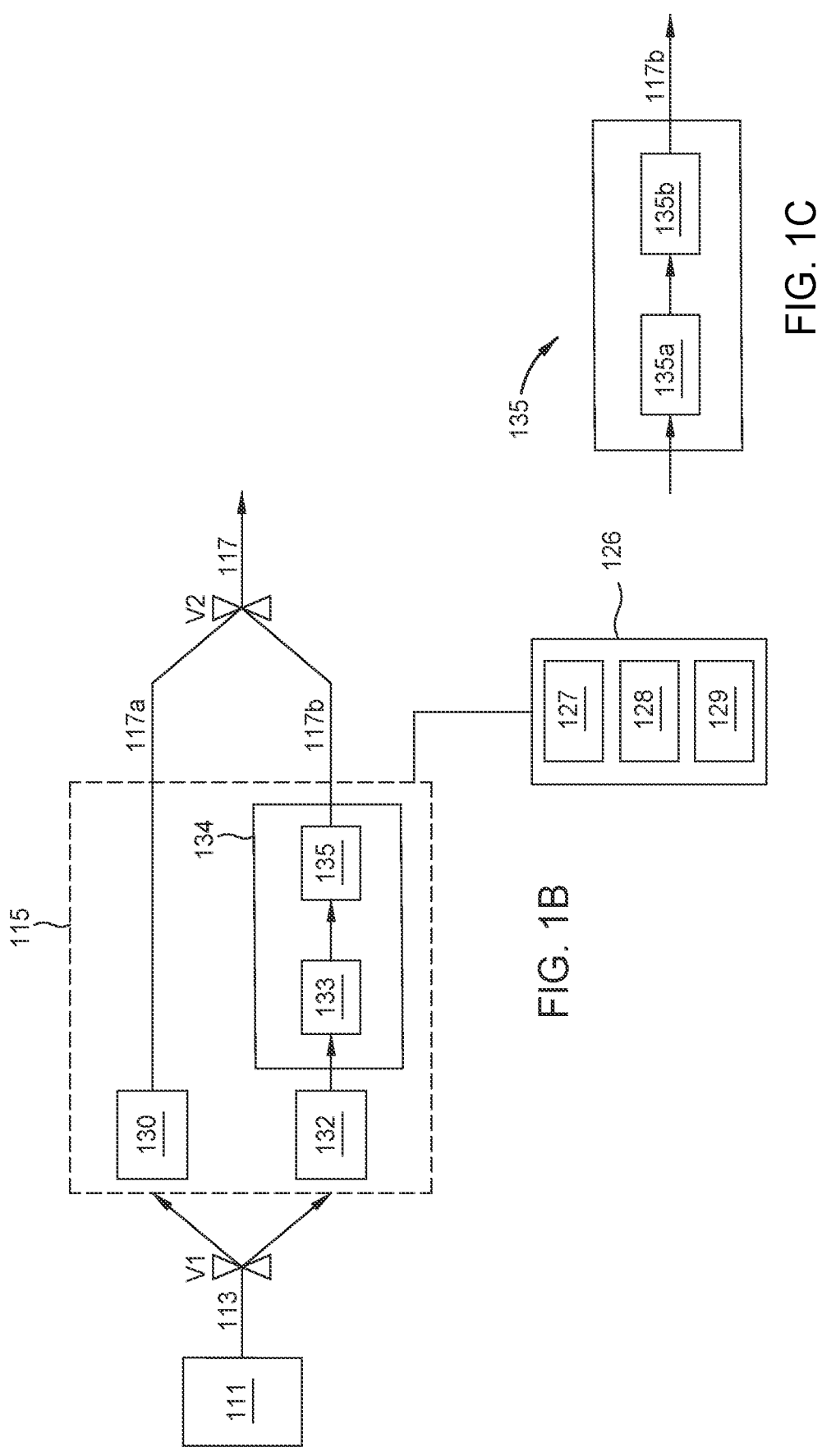
FIG. 1B is an example syngas conversion unit of the apparatus shown in FIG. 1A according to at least one aspect of the present disclosure.
FIG. 1C is an example oligomerization unit of the syngas conversion unit shown in FIG. 1B according to at least one aspect of the present disclosure.

The apparatus 100 includes a drying unit 103 coupled at a first end with a first end of a gasification unit 111. The drying unit 103 is also coupled at a second end with a first end of a hydrotreatment unit 107. A second end of the gasification unit 111 is coupled to a first end of a syngas conversion unit 115 (e.g., a Fischer-Tropsch unit 130, and/or a fermentation unit 132 coupled to an ethanol conversion unit 134, as shown in FIG. 1B).

A second end of the hydrotreatment unit 107 is coupled to a first end of a collection unit 119. In addition, a second end of the syngas conversion unit 115 is coupled to a second end of the collection unit 119. As discussed below, the drying unit 103 is configured to convert the carbon-containing feedstock comprising, e.g., forest residues, to a dried carbon-containing material 105b; the gasification unit 111 is configured to convert the dried carbon-containing material 105b to a conversion product such as a syngas 113.

In operation, the carbon-containing feedstock 101 enters the drying unit 103 through line 102. In the drying unit 103, the carbon-containing feedstock 101 is converted to a terpene stream 105a and the dried carbon-containing material 105b as discussed below. The terpene stream 105a is fed to the hydrotreatment unit 107 via line 106a and the dried carbon-containing material 105b is fed to the gasification unit 111. A hydrotreating agent 123 (e.g., hydrogen gas) enters the hydrotreatment unit 107 via line 124 to convert the terpene stream 105a to a first hydrocarbon stream 109 in the presence of a hydrotreatment catalyst located in hydrotreatment unit 107. The first hydrocarbon stream 109 can include, e.g., jet fuel, diesel fuel, or a combination thereof. The first hydrocarbon stream 109 is then fed to the collection unit 119 through line 110. The collection unit 119 can be a storage tank, a pipeline, a tank truck, a rail car, or another suitable means to store and/or transport the first hydrocarbon stream 109. The collection unit 119 can also be used to blend or otherwise mix the first hydrocarbon stream 109 with another stream, e.g., a second hydrocarbon stream 117 discussed below.

The dried carbon-containing material 105b enters the gasification unit 111 via line 106b. A gasification agent 121 (e.g., steam, oxygen, and/or air) is flowed from a gasification agent unit 104 to the gasification unit 111 through line 122. In the gasification unit 111, the dried carbon-containing material 105b and the gasification agent 121 are heated and undergo a gasification reaction to form the syngas 113 (or synthesis gas or synthetic gas). Syngas is a gas mixture that includes $H_2$ and carbon monoxide (CO), and oftentimes includes other components such as carbon dioxide ($CO_2$).

The syngas 113 flowing out of the gasification unit 111 can be at an elevated temperature, for example, about 700° C. or more, such as from about 700° C. to about 1200° C. One or more heat exchangers in the line 112 between the gasification unit 111 and the syngas conversion unit 115. Similarly, one or more heat exchanges can be along various other lines of apparatus 100. The syngas 113 flowing out of the gasification unit 111 can contain undesirable levels of water, particulate solids, and/or contaminants (e.g., sulfur, selenium, phosphorus, arsenic, nitrogen, carbon dioxide, and/or halogen). The concentrations of the water, particulate solids, and/or contaminants may be reduced using one or more gas-liquid sorption devices, temperature swing adsorption devices, pressure swing adsorption devices, microchannel devices, cyclones, condensers, etc., in the line 112 between the gasification unit 111 and the syngas conversion unit 115. Similarly, one or more these apparatus can be along various other lines of apparatus 100.

As shown in FIG. 1B, the syngas 113 flows from the gasification unit 111 into the syngas conversion unit 115 through line 112. In the syngas conversion unit 115, the syngas 113 is converted into hydrocarbon(s) 117a in the presence of a Fischer-Tropsch catalyst in a Fischer-Tropsch unit 130 as described below. Additionally, or alternatively, the syngas 113 is fed to a fermentation unit 132 to form ethanol and the ethanol is fed to an ethanol conversion unit 134 to form the hydrocarbon(s) 117b. The ethanol conversion unit can include a dehydration unit 133 to convert ethanol to ethylene coupled to an oligomerization unit 135 to oligomerize ethylene into hydrocarbon(s) 117b. The hydrocarbon(s) 117a and hydrocarbon(s) 117b can be combined into a single stream, e.g., second hydrocarbon stream 117, if desired. This can be performed through operation of a valve V2. As shown in FIG. 1B, a valve V1 can be operated such that syngas 113 can be flowed to the Fischer-Tropsch unit 130 and/or the fermentation unit 132.

The hydrocarbon(s) 117a and/or 117b, collectively the second hydrocarbon stream 117, produced from the syngas conversion unit 115 can include, e.g., jet fuel, diesel fuel, or a combination thereof. The second hydrocarbon stream 117 is then fed to the collection unit 119 through line 116. The collection unit 119 can be a storage tank, a pipeline, a tank truck, a rail car, or another suitable means to store and/or transport the second hydrocarbon stream 117. The collection unit 119 can also be used to blend or otherwise mix the second hydrocarbon stream 117 with another stream, e.g., first hydrocarbon stream 109. The combined first hydrocarbon stream 109 and the second hydrocarbon stream 117 is referred to as a fuel composition 120.

Referring back to FIG. 1A, and in some aspects, the hydrotreating agent 123 can be produced by electrolysis in electrolysis unit 125. The electrolysis unit 125 is coupled at a first end to a third end of the hydrotreatment unit 107 via line 124. In the electrolysis unit, the hydrotreating agent 123 (e.g., hydrogen gas) can be produced by the electrolysis of water according to known methods. In this process, water is decomposed into hydrogen gas ($H_2$) and oxygen gas ($O_2$) by electrochemical reactions at the electrodes of an electrolytic cell. Additionally, or alternatively, the hydrotreating agent 123 (e.g., hydrogen gas) can be produced by steam-methane reforming with carbon capture, hydrogen generation via plasma electrolysis, biomass gasification, and/or by other suitable methods having lower carbon intensity relative to 'traditional' steam methane reforming. Traditional steam methane reforming is when methane comes from fossil sources and there are no carbon capture methods included. Non-traditional steam-methane reforming refers to methane produced from non-fossil based sources (e.g., renewable natural gas) or from fossil-based sources further coupled with carbon capture methods. In steam-methane reforming, steam reacts with methane under suitable pressures and in the presence of a catalyst to generate hydrogen. With respect to plasma electrolysis, the electrodes in plasma electrolysis systems are not immersed in water to produce $H_2$ and $O_2$. Gasification is discussed below. Here, a portion of the $H_2$ produced during gasification can be used as the hydrotreating agent 123 by, e.g., feeding the $H_2$ directly or indirectly to the hydrotreatment unit 107.

It is contemplated that one or more of the elements described in FIG. 1A may be coupled to controller 126. The controller 126 is utilized to control one or more operating parameters of the one or more elements as described below. The controller 126 includes a processor 127, memory 128, and support circuits 129. The processor 127 may be one of any form of general purpose microprocessor, or a general purpose central processing unit (CPU), each of which can be used in an industrial setting, such as a programmable logic controller (PLC), supervisory control and data acquisition (SCADA) systems, or other suitable industrial controller.

The memory 128 is non-transitory and may be one or more of readily available memory such as random access memory (RAM), read only memory (ROM), or any other form of digital storage, local or remote. The memory 128 contains instructions, that when executed by the processor 127, facilitates the operation the apparatus of FIGS. 1A, 1B, and 3, and the operations of process 200. The instructions in the memory 128 are in the form of a program product such as a program that implements the method of the present disclosure. The program code of the program product may conform to any one of a number of different programming languages. Illustrative computer-readable storage media include, but are not limited to: (i) non-writable storage media (e.g., read-only memory devices within a computer such as CD-ROM disks readable by a CD-ROM drive, flash memory, ROM chips, or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer-readable storage media, when carrying computer-readable instructions that direct the functions of the methods described herein, are examples of the present disclosure. In one example, the disclosure may be implemented as the program product stored on a computer-readable storage media (e.g., memory 128) for use with a computer system (not shown). The program(s) of the program product define functions of the disclosure, described herein.

Figure 3:
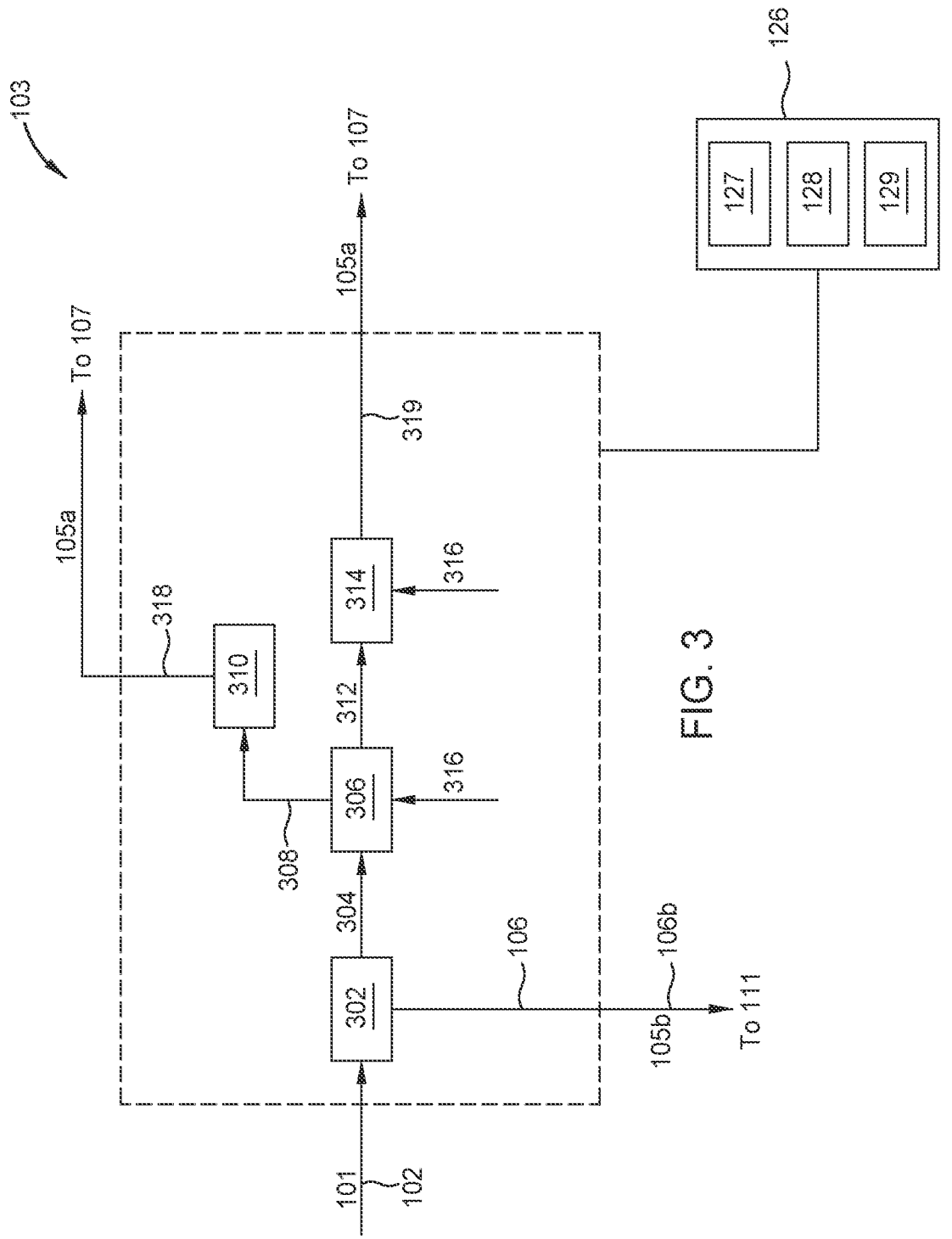
FIG. 3 is an example drying unit of the apparatus shown in FIG. 1A according to at least one aspect of the present disclosure.

Although not shown in FIG. 1A, 1B, IC and FIG. 3 (discussed later), it should be understood that equipment for controlling, e.g., temperature, pressure, and flow control of various feeds can be used with the apparatus 100. For example, heat exchangers can be used to cool or heat a liquid or a gas along the feed lines or within various units of the apparatus 100, while pumps and motors can be utilized to control the rate of flow of the materials and the operating pressures in apparatus 100. Further, apparatus 100 may include features for facilitating separation and/or purification of components as well as valves or other release mechanisms for, e.g., purging gases or liquids from the system. Various process controls can be used. Such process controls can include probes and sensors such as pressure indicators, differential pressure cells, temperature indicators, thermocouples, temperature switches, resistance temperature detectors, solenoids, flowmeters, flow regulators and valves, gas analyzers, humidity sensors, radar sensors, ammeters, current meters, liquid level detectors, feed level probes, electrical drives, and combinations thereof.

FIG. 2 shows selected operations of a process 200 for converting a carbon-containing feedstock to a hydrocarbon product according to at least one aspect of the present disclosure. The hydrocarbon product can be a fuel composition or an additive to be used in a fuel composition. The process 200 can be performed by apparatus 100, though modifications of the apparatus 100 are contemplated. It is contemplated that one or more of the operations described in FIG. 2 may be controlled by controller 126. The controller is utilized to control one or more operating parameters of the one or more elements.

The process 200 includes drying a carbon-containing feedstock, e.g., carbon-containing feedstock 101 (which can include biomass), to form the terpene stream 105a and the dried carbon-containing material 105b at operation 210. The drying process of operation 210 can be performed using suitable apparatus and methods.

For operation 210, a drying unit (e.g., drying unit 103) is utilized to dry the carbon-containing feedstock 101. Referring to FIG. 3, as the carbon-containing feedstock 101 is heated during the drying process in a dryer 302 of drying unit 103, the carbon-containing feedstock 101 releases, e.g., volatile organic compounds (including terpenes), their thermal decomposition products, and/or particulate matter in an exhaust stream 304. The volatile organic compounds released in the exhaust stream 304 include terpenes, terpenoids, isomers thereof, and derivatives thereof, among other compounds and components. The dryer 302 can be any suitable apparatus for drying the carbon-containing feedstock 101 such as an oven, kiln, rotary dryer, flash-tube dryer, or combinations thereof.

In some aspects, the terpene stream 105a is isolated from the exhaust stream 304 by use of, e.g., a sorbent located in an adsorber unit 306 to trap terpenes from the exhaust stream 304. A gaseous stream 308 comprising terpenes can then be released from the sorbent by, e.g., thermal control (e.g., use of heaters, condensers, and/or chilling equipment), solvent extraction, supercritical $CO_2$ desorption, and/or steam stripping. For example, the sorbent having terpenes adsorbed thereto can be heated to a temperature suitable for release of the terpenes in the gaseous stream 308. The gaseous stream 308 can then be condensed to a liquid in a condenser unit 310. In the condenser unit 310, the gaseous stream 308 contacts cooled condenser coils, and the liquid condensate comprising the terpene stream 105a can be collected. Additionally, or alternatively, the sorbent 312 (having the terpenes adsorbed thereto) can be fed to a desorber unit 314. In the desorber unit 314, desorbers can be utilized to release the terpene stream 105a comprising terpenes from the sorbent. A non-reactive (or inert) carrier gas 316, such as $N_2$, can be flowed into the adsorber unit 306 to aid in adsorption of the terpenes to the sorbent. Additionally, the non-reactive (or inert) carrier gas 316, such as $N_2$, can be flowed into the desorber unit 314 to aid the release of the terpene stream from the sorbent. The non-reactive gas also provides a non-reactive (or inert) environment as, e.g., the sorbent is heated.

Operating conditions, e.g., temperature, pressure, velocity, and/or other process parameters, of the drying unit 103 (including the dryer 302, the adsorber unit 306, the desorber unit 314, etc.) can be selected or controlled such that the terpene streams 105a are suitably collected from the carbon-containing feedstock 101. The operating conditions can also be chosen to remove water from the carbon-containing feedstock 101 and/or the terpene stream 105a.

A residence time of the sorbent, having terpenes adsorbed thereto, within the desorber unit 314 can be more than about 5 minutes and/or less than about 40 hours, such as from about 0.5 h to about 36 h, such as from about 1 h to about 24 h, such as from about 2 h to about 12 h, such as from about 4 h to about 8 h, though other values are contemplated. The operating temperature of the desorber unit 314 can be set to about 450° C. or less, such as from about 150° C. to about 400° C., such as from about 175° C. to about 375° C., such as from about 200° C. to about 350° C., such as from about 225° C. to about 325° C., such as from about 250° C. to about 300° C., though other values are contemplated. A flow rate of the non-reactive carrier gas into the desorber unit 314 can be at least about 1 cubic foot per minute (cfm), such as from about 1 cfm to about 25 cfm, such as from about 2 cfm to about 20 cfm, such as from about 5 cfm to about 15 cfm, though other values are contemplated. The desorber unit 314 can be operated at a pressure of 250 Pascal (Pa) to about 30,000 Pa, such as from about 2,500 Pa to about 25,000 Pa, such as from about 5,000 Pa to about 20,000 Pa, such as from about 10,000 Pa to about 15,000 Pa, though other values are contemplated.

The volume of the exhaust stream 304 fed to the adsorber unit 306 can be from about 85 cubic meter per hour (cmh) to about 850,000 cmh, such as from about 1,500 cmh to about to about 700,000 cmh, such as from about 15,000 cmh to about 500,000 cmh, such as from about 150,000 cmh to about 300,000 cmh. In some aspects, the volume of the exhaust stream 304 fed to the adsorber unit 306 can be from about 50 cmh to about 350,000 cmh, such as from about 100 cmh to about 200,000 cmh, such as from about 500 cmh to about 100,000, such as from about 1,000 cmh to about 50,000 cmh, such as from about 5,000 cmh to about 25,000 cmh, though other values are contemplated.

After exiting condenser unit 310 and/or the desorber unit 314, the terpene stream 105a can be subjected to distillation, filtration, cleaning, stripping, flashing, bubbling with a non-reactive gas (e.g., $N_2$), and/or other suitable processes along lines 318, 319 to remove undesired components and isolate the terpene stream 105a.

The terpene stream 105a produced from drying unit 103 can include alpha-pinene (α-pinene), beta-pinene (β-pinene), β-carene, dipentene, camphene, limonene, o-cymene, p-cymene, α-terpineol, cis-β-terpineol, trans-β-terpineol, gamma-terpineol (γ-terpineol), fenchene, α-fenchene, p-allylanisole, tricyclene, p-xylene, vinylcyclohexene, 2-norpinene, terpilene, p-cymenene, fenchol, myrcene, terpinolene, cis-anethole, trans-anethole, caryophyellenes, α-phellandrene, β-phellandrene, methyl chavicol, tricyclene, 1,4-cineole, 1, β-cineole, α-terpinene, γ-terpinene, isoterpinolene, camphor, L-camphor, isoborneol, borneol, L-borneol, cis-1, β-terpin, trans-1, β-terpin, camphenilone, fenchone, exo-fenchol, exo-2,7,7-trimethylbicyclo [2.2.1] heptan-2-ol, fenchyl acetate, borneol acetate, isomers thereof, derivatives thereof, and/or combinations thereof.

In some aspects, the terpene stream 105a is substantially composed of terpenes having the formula $(C_5H_8)_n$, where is an integer such as 2, 3, 4, 5, 6, 7, 8, etc. The terpene stream 105a can be composed of, or substantially composed of, monoterpenes $(C_{10}H_{16})$. In some aspects, the terpene stream 105a includes α-pinene, β-pinene, β-carene, dipentene, camphene, isomers thereof, derivatives thereof, or combinations thereof. The terpene stream 105a can also include other hydrocarbons (as well as substituted hydrocarbons where a hydrogen and/or carbon is replaced with a heteroatom).

The composition of the terpene stream 105a can be controlled by, e.g., adjusting various operating parameters of the drying unit 103. An amount of α-pinene in the terpene stream 105a can be from about 0 wt % to about 100 wt %, such as from about 10 wt % to about 90 wt %, such as from about 20 wt % to about 80 wt %, such as from about 30 wt % to about 70 wt %, such as from about 40 wt % to about 60 wt %, such as from about 45 wt % to about 55 wt %, based on the total weight of the terpene stream 105a, though other values are contemplated. In some aspects, the amount of α-pinene in the terpene stream 105a can be less than about 50 wt %, such as from about 0 wt % to about 50 wt %, such as from about 1 wt % to about 45 wt %, such as from about 10 wt % to about 40 wt %, such as from about 20 wt % to about 30 wt %, based on the total weight of the terpene stream 105a, though other values are contemplated.

Additionally, or alternatively, and in some aspects, an amount of β-pinene in the terpene stream 105a can be from about 0 wt % to about 100 wt %, such as from about 10 wt % to about 90 wt %, such as from about 20 wt % to about 80 wt %, such as from about 30 wt % to about 70 wt %, such as from about 40 wt % to about 60 wt %, such as from about 45 wt % to about 55 wt %, based on the total weight of the terpene stream 105a, though other values are contemplated. In some aspects, the amount of β-pinene in the terpene stream 105a can be less than about 50 wt %, such as from about 0 wt % to about 50 wt %, such as from about 1 wt % to about 45 wt %, such as from about 10 wt % to about 40 wt %, such as from about 20 wt % to about 30 wt %, based on the total weight of the terpene stream 105a, though other values are contemplated.

A total amount of α-pinene and β-pinene in the terpene stream 105a can be about 0 wt % or more, such as about 1 wt % or more, such as about from about 10 wt % to about 90 wt %, such as from about 20 wt % to about 80 wt %, such as from about 30 wt % to about 70 wt %, such as from about 40 wt % to about 60 wt %, such as from about 45 wt % to about 55 wt %, based on the total weight of the terpene stream 105a, though other values are contemplated. In some aspects, the total amount of α-pinene and β-pinene in the terpene stream 105a in the terpene stream 105a can be about 50 wt % or more, such as from about 50 wt % to about 99 wt %, such as from about 51 wt % to about 95 wt %, such as from about 60 wt % to about 90 wt %, such as from about 70 wt % to about 80 wt %, based on the total weight of the terpene stream 105a, though other values are contemplated.

The terpene stream 105a, whether at least partially purified or not, can then be fed to the hydrotreatment unit 107, while the dried carbon-containing material 105b can be fed to gasification unit 111 through line 107 and the line 106b.

The process 200 further includes hydrotreating the terpene stream 105a to form the first hydrocarbon stream 109 at operation 220. The hydrotreatment of operation 220 can be performed in a hydrotreatment unit (e.g., hydrotreatment unit 107). In the hydrotreatment unit 107, the terpene stream 105a is introduced to the hydrotreating agent 123, e.g., hydrogen gas, and a hydrotreatment catalyst. Products produced from the process 200 include alkanes such as pinane (via hydrogenation of pinene, e.g., α-pinene and/or β-pinene).

The hydrotreatment process of operation 220 can be performed by suitable methods and suitable hydrotreatment catalysts. Catalysts useful for hydrotreating compounds in the terpene stream 105a include those that are capable of hydrotreating one or more olefinic bonds of compounds in the terpene stream 105a. The hydrotreatment catalysts include a metal such as platinum (Pt), palladium (Pd), cobalt (Co), molybdenum (Mo), nickel (Ni), rhodium (Rh), ruthenium (Ru), chromium (Cr), iridium (Ir), and combinations thereof. The metal can have various ligands such as oxygen, CO, halogen, N-heterocyclic carbene (NHC), alkylene, 1,5-cyclooctadiene (COD), arylene, triphenylphosphine (PPh$_3$), and combinations thereof. Illustrative, but non-limiting, examples of hydrotreatment catalysts include Ni—NHC, CoO/MoO$_3$, NiO/MoO$_3$, and mixtures thereof. The hydrotreatment catalyst can be on a support such as carbon, SiO$_2$, Al$_2$O$_3$, SiO$_2$/Al$_2$O$_3$, calcium carbonate (CaCO$_3$), titanium dioxide (TiO$_2$), barium sulfate (BaSO$_4$), and/or zeolites. The hydrotreatment operation can be performed in the hydrotreatment unit 107. In some aspects, product(s) produced from the hydrogenation process can be reintroduced to the terpene stream 105a flowing into the hydrotreatment unit 107 to increase the amount of alkenes/olefins reduced to alkanes.

The pressure utilized for the hydrotreatment process of operation 220 can be about 0.1 megapascal (MPa) or more, such as from about 1 bar to about 20 MPa, such as from about 1.5 MPa to about 15 MPa, such as from about 2 MPa to about 10 MPa, such as from about 2.5 MPa to about 7.5 MPa, such as from about 3 MPa to about 5 MPa, though other values are contemplated. The temperature for the hydrotreatment process of operation 220 can be about 50° C. or more, such as about 80° C. or more, such as about 100° C. or more, such as about 150° C. to about 500° C., such as from about 175° C. to about 450° C., such as from about 200° C. to about 425° C., such as from about 250° C. to about 400° C., such as from about 275° C. to about 400° C., such as from about 300° C. to about 375° C., such as from about 325° C. to about 350° C., though other values are contemplated. In some aspects, a flow ratio of hydrotreating agent 123/terpene stream 105a is from about 50 normal liter per liter (NL/L) to about 2,500 NL/L, such as from about 75 NL/L to about 2,000 NL/L, such as from about 100 NL/L to about 500 NL/L, such as from about 125 NL/L to about 400 NL/L, such as from about 150 NL/L to about 300 NL/L, though other values are contemplated.

The product stream(s) formed from the hydrotreatment process of operation 220 includes the first hydrocarbon stream 109. The first hydrocarbon stream 109 can include one or more hydrocarbon components, such as jet fuel, diesel fuel, gasoline, naphtha, or combinations thereof, such as jet fuel, diesel fuel, or combinations thereof.

Process 200 further includes gasifying the dried carbon-containing material 105b to form the syngas 113 (e.g., CO and H$_2$) at operation 230. Gasification generally involves converting organic material, e.g., biomass, into gaseous compounds such as syngas, by reacting the feed at high temperatures (about 700° C. or more) and controlling the amount of O$_2$, steam, and/or air present in the reaction. Here, the gasification agent 121 (e.g., steam, oxygen, and/or air) and the dried carbon-containing material 105b are heated to undergo a gasification reaction to form the syngas 113. The gasification process of operation 230 can be performed in gasification unit 111 by suitable methods.

The gasification unit 111 can include one or more gasifiers to combust, or at least partially combust, the dried carbon-containing material 105b. Various types of gasifiers can be used including fluidized-bed gasifiers (such as circulating fluidized bed, dual fluidized bed, and bubbling fluidized bed), entrained flow gasifiers, plasma gasifiers, free radical gasifiers, counter-current fixed bed gasifiers, and/or co-current fixed bed gasifiers. Prior to gasification, the dried carbon-containing material 105b can be crushed into small particles (e.g., less than about 100 mm or less than about 50 mm, such as between about 5 mm and about 20 mm) to provide, e.g., a larger surface area for the gasification reaction. Crushing the dried carbon-containing material 105b can be performed by any suitable apparatus such as grinding or shearing.

In operation, the dried carbon-containing material 105b (and/or small particles thereof) can be fed to the gasifier located in gasification unit 111 by, e.g., a lock hopper and/or a screw feeder. The gasification agent 121 is fed from gasification agent unit 104 to the gasifier located in the gasification unit 111 through the line 122. Depending on the gasifier utilized, a slurry material and/or a bed material that includes, e.g., dolomite, limestone, sand, calcium-containing materials, or combinations thereof, is present in the gasifier located in gasification unit 111. After a suitable residence time and under conditions effective to gasify the dried carbon-containing material 105b, the syngas 113 comprising H$_2$ and CO is produced. The gasifier located in gasification unit 111 can also contain metal-based catalysts, where the metal is Ni, Rh, Ru, Ir, Pt, Pd, Cu, Co, Fe, or combinations thereof, to convert by-products of syngas production (e.g., methane and tar) to CO and H$_2$. These catalysts for catalytic treatment can be on a support such as SiO$_2$, Al$_2$O$_3$, ZrO$_2$, Ce$_2$O$_3$, TiO$_2$, and/or sand, and the catalysts can be promoted with Mn, Mo, Ti, Zr, Ag, Rh, and/or Sn. Temperatures for the catalytic treatment of methane (CH$_4$) and tar can be from about 900° C. to about 1500° C., such as from about 1000° C. to about 1200° C. Operating temperatures of the gasifier(s) of the gasification unit 111 can be more than about 200° C. (e.g., the temperature where pyrolysis occurs), such as more than about 300° C., such as more than about 400° C., such as from about 600° C. to about 900° C., such as from about 650° C. to about 850° C., such as from about 700° C. to about 800° C., such as about 700° C. to about 710° C., about 710° C. to about 720° C., about 720° C. to about 730° C., about 730° C. to about 740° C., about 740° C. to about 750° C., about 750° C. to about 760° C., about 760° C. to about 770° C., about 770° C. to about 780° C., about 780° C. to about 790° C., or about 790° C. to about 800° C., though other values are contemplated. The gasifier(s) of the gasification unit 111 can be set at a pressure below about 1.1 MPa, such as below about 0.5 MPa, such as below about 0.2 MPa, such as below about 0.15 MPa, such as below about 0.1 MPa (below about ~1 atm), though other values are contemplated.

An amount of $O_2$ introduced into the gasifier of the gasification unit 111 can be from about 0 to about 100 lb-moles per ton of dried carbon-containing material 105*b* on a dry basis. In various aspects, the amount of $O_2$ introduced into the gasifier can be from about 5 to about 75, 10 to about 70, such as from about 20 to about 60, such as from about 30 to about 50, such as from about 40 to about 45 lb-moles per ton of dried carbon-containing material 105*b* on a dry basis, though other values are contemplated. An amount of steam introduced into the gasifier of the gasification unit 111 can be from about 0 to about 75 lb-moles per ton of dried carbon-containing material 105*b* on a dry basis. In various aspects, the amount of steam introduced into the gasifier can be from about 0 to about 50, such as from about 5 to about 45, such as from about 10 to about 40, such as from about 20 to about 30 lb-moles per ton of dried carbon-containing material 105*b* on a dry basis, though other values are contemplated.

The syngas 113 can have a molar ratio of $H_2$ to CO that is from about 0.25:1 to about 3:1, such as from about 0.5:1 to about 2.5:1, such as from about 0.75:1 to about 2.25:1, such as from about 1:1 to about 2:1, from about 1.5:1 to about 2:1, or from about 1.8:1 to about 2.2:1. In at least some aspects, the syngas has a molar ratio of $H_2$ to CO that is from about 1.8:1 to about 2.1:1. Other values for the molar ratio of $H_2$ to CO are contemplated.

Process 200 further includes converting the syngas 113 to a second hydrocarbon stream 117 at operation 240. Operation 240 can be performed in the syngas conversion unit 115. As shown in FIG. 1B, the syngas conversion unit 115 can be (or include) a Fischer-Tropsch unit 130 where the syngas 113 undergoes a Fischer-Tropsch process. Here, the Fischer-Tropsch process of operation 240 converts the syngas 113 comprising $H_2$ and CO into hydrocarbon(s) 117*a* in the presence of a Fischer-Tropsch catalyst located in the Fischer-Tropsch unit 130. The hydrocarbon(s) 117*a* can form at least a portion of the second hydrocarbon stream 117. The Fischer-Tropsch process of operation 240 can be performed by suitable methods.

For the Fischer-Tropsch process, the Fischer-Tropsch unit 130 can include one or more reactors such as entrained-flow reactors, slurry reactors, fluid-bed reactors, circulating catalyst reactors, and/or tubular fixed-bed reactors. Examples of suitable Fischer-Tropsch catalysts can include a supported or unsupported metal such as Co, Fe, Ru, W, and/or Ni, with or without a promoter. The Fischer-Tropsch catalyst can optionally include a ligand such as sulfide, hydroxide, oxide, CO, cyclopentadienyl (Cp), bipyridyl, 2-aminopyridine, 2-amino phenol, 2-imino pyridine, sodium anthranilate, potassium anthranilate, or combinations thereof. The catalyst can be supported on, e.g., $SiO_2$, $Al_2O_3$, $TiO_2$, and/or zeolites. Various promoters can be utilized to, e.g., enhance the activity of the catalyst. Illustrative, but non-limiting, examples of promoters include carbides, metal or metal containing materials (e.g., Ru-, Rh-, Zr-, Cu-, Mn-, Ce-, Pt-, Ir-, Mo-, or W-containing materials), and/or oxides (such as metal oxides, metal hydroxides, or salts of Li, Na, K, Rb, Cs, Mg, Sr, Th, such as potassium oxide ($K_2O$)). The syngas 113 flowing into the Fischer-Tropsch unit 130 can include a mixture of $H_2$ and CO, wherein $H_2$ and CO are present in a molar ratio of about 0.5:1 or more, such as about 1:1 or more, such as about 1.7:1 or more, such as about 1.75:1 to about 2.5:1, such as about 1.8:1 to about 2.2:1 or from about 1.8:1 to about 2.1:1. Higher or lower ratios are contemplated.

In operation, for example, the syngas 113 stream is fed to Fischer-Tropsch unit 130. Here, the syngas 113 is introduced with the Fischer-Tropsch catalyst such that the syngas 113 contacts the Fischer-Tropsch catalyst. After a suitable residence time and under conditions effective to convert the syngas 113, hydrocarbon(s) are produced. Operating temperatures for the Fischer-Tropsch unit 130 can be more than about 125° C., such as from about 150° C. to about 350° C., such as from about 175° C. to about 325° C., such as from about 200° C. to about 300° C., such as from about 225° C. to about 275° C. The Fischer-Tropsch unit 130 can be set at a pressure ranging from about 100 kilopascal (kPa) to about 10 MPa, such as about 4 MPa or less, such as from about 1 MPa to about 3.5 MPa, such as from about 1.5 MPa to about 3 MPa, such as from about 2 MPa to about 2.5 MPa. In at least one aspect, the pressure of the Fischer-Tropsch unit 130 is from about 2.1 MPa to about 3.5 MPa (about 300 pound per square inch gauge (psig) to about 500 psi) and the temperature is from about 150° C. to about 300° C. Other operating parameters of the Fischer-Tropsch unit 130 are contemplated.

Typical reaction products made in the Fischer-Tropsch unit 130 include alkane(s) (primary reaction product(s)), as well as olefins, oxygenates, substituted hydrocarbons (hydrocarbons containing one or more heteroatoms different from carbon and hydrogen) The second hydrocarbon stream 117 produced from the Fischer-Tropsch process can be used directly for the fuel composition 120

Additionally, or alternatively, operation 240 can include conversion of the syngas 113 to an alcohol (e.g., ethanol) followed by conversion of the ethanol into hydrocarbon(s) 117*b*. The hydrocarbon(s) 117*b* can form at least a portion of the second hydrocarbon stream 117. This conversion of the syngas 113 to the second hydrocarbon stream 117 can include fermentation of the syngas 113 in the fermentation unit 132 (FIG. 1B) to form ethanol, dehydration of the ethanol to form ethylene in the dehydration unit 133, and a two-operation oligomerization process in the oligomerization unit 135. The two-operation oligomerization process in the oligomerization unit 135 can include a first oligomerization of ethylene to form a first olefin product (e.g., $C_3$-$C_8$ olefin(s)), and a second oligomerization of the first olefin product to form a second olefin product, e.g., the second hydrocarbon stream 117. Additionally, or alternatively, the conversion of syngas 113 to the second hydrocarbon stream 117 can include fermentation of the syngas 113 to form ethanol, and performing a "one-operation" dehydration-oligomerization process on the ethylene to form the second hydrocarbon stream 117. The latter one-operation dehydration-oligomerization process can include a catalyst that both dehydrates ethanol to ethylene and oligomerizes the ethylene to hydrocarbons.

In such aspects, the syngas 113 can be fed to a syngas conversion unit 115 that includes a fermentation unit 132 and an ethanol conversion unit 134 (FIG. 1B). The syngas 113 is introduced with a microorganism to convert the syngas 113 to ethanol in the fermentation unit 132, and the ethanol conversion unit 134 converts ethanol to hydrocarbon(s) 117b. Illustrative, non-limiting, examples of microorganisms useful for the fermentation in the fermentation unit 132 include *Moorella*, *Clostridium* (e.g., *Clostridium autoethanogenum*), *Ruminococcus*, *Acetobacterium*, *Eubacterium*, *Butyribacterium*, *Oxobacter*, *Methanosarcina*, *Methanosarcina*, and *Desulfotomaculum*, or combinations thereof that convert the syngas 113 to alcohols (e.g., ethanol). Fermentation of the syngas 113 in the fermentation unit 132 can be performed at temperatures of about 30° C. to about 50° C., such as from about 35° C. to about 45° C., and at a pressure about atmospheric pressure or higher about atmospheric pressure or at a pressure of about atmospheric pressure. Other operating parameters of the fermentation unit 132 are contemplated. The fermentation typically produces a fermentation broth from which ethanol can be separated by suitable methods.

The ethanol produced from fermentation can then be converted to hydrocarbon products in an ethanol conversion unit 134. The ethanol conversion unit 134 converts ethanol to the hydrocarbon(s) 117b. In some aspects, the ethanol conversion unit 134 includes a dehydration unit 133 and an oligomerization unit 135. Any suitable method for ethanol conversion can be used such as a two-operation oligomerization process or a one-operation dehydration-oligomerization process.

Prior to the two-operation oligomerization process, the ethanol flowing from fermentation unit 132 is converted to ethylene in the dehydration unit 133 under conditions effective to form ethylene. The dehydration unit 133 includes a dehydration catalyst (e.g., alumina, modified alumina, $SiO_2$/ $Al_2O_3$, β-type zeolites, ZSM-5 zeolites, Y-type zeolites, fluoride-treated β-zeolite catalysts, fluoride-treated clay catalysts, etc.), sulfonic acid resins (e.g., sulfonated styrene resins such as Amberlyst® 15), phosphoric acid, sulfuric acid, Lewis acids such boron trifluoride and aluminum trichloride, and many different types of metal salts including metal oxides (e.g., zirconium oxide or titanium dioxide). Here, the ethanol can be fed to the dehydration unit 133, where it is introduced to the dehydration catalyst. The operating temperature of the dehydration unit 133 can be from about 150° C. to about 550° C., such as from about 200° C. to about 500° C., such as from about 250° C. to about 450° C., such as from about 300° C. to about 400° C., though other temperatures are contemplated. The dehydration unit 133 can be set to a pressure from about 0 psig to about 1500 psig, such as from about 5 psig to about 1200 psig, such as from about 10 psig to about 500 psig, such as from about 50 psig to about 250 psig, though other pressures are contemplated. The ethanol or ethanol-containing feedstock can be fed from the fermentation unit 132 to the dehydration unit 133 with a weight hourly space velocity (WHSV) value that is from about 0.05 h$^{-1}$ to about 30 h$^{-1}$, such as from about 0.1 h$^{-1}$ to about 15 h$^{-1}$, such as from about 0.2 h$^{-1}$ to about 10 h$^{-1}$, such as from about 0.5 h$^{-1}$ to about 5 h$^{-1}$, though other values are contemplated.

The ethylene produced in the dehydration unit 133 is then fed to a first oligomerization reactor 135a of the oligomerization unit 135 where the ethylene is converted to a first oligomerization product by using a metal-supported catalyst (e.g., Cr, Ti, Zr, and/or Ni on a solid support such as $SiO_2$, $Al_2O_3$, $TiO_2$, and/or zeolites). Various promoters and/or activators can be utilized to, e.g., enhance the activity of the catalyst, such as alkylaluminum-based compounds, e.g., trialkylaluminum, methylaluminoxane (MAO), and/or modified methylaluminoxane (MMAO). The first oligomerization product can be a hydrocarbon having a carbon number from about C3 to C8, such as a $C_3$-$C_8$ olefin, such as propylene, butene(s), pentene(s), hexene(s), heptene(s), and/or octene(s). The first oligomerization reactor 135a can be one reactor, parallel reactors, and/or multiple sequential reactors. The operating temperature of the first oligomerization reactor 135a can be less than about 250° C., such as from about 50° C. to about 225° C., such as from about 75° C. to about 200° C., such as from about 100° C. to about 175° C., such as from about 125° C. to about 150° C. The first oligomerization reactor 135a can be set to a pressure from about 0 psig to about 1500 psig, such as from about 5 psig to about 1200 psig, such as from about 10 psig to about 500 psig, such as from about 50 psig to about 250 psig. The ethylene or ethylene-containing feedstock can be fed to the first oligomerization reactor 135a with a WHSV value that is from about 0.05 h$^{-1}$ to about 300 h$^{-1}$, such as from about 0.1 h$^{-1}$ to about 150 h$^{-1}$, such as from about 0.2 h$^{-1}$ to about 100 h$^{-1}$, such as from about 0.5 h$^{-1}$ to about 5 h$^{-1}$. Other operating parameters of the first oligomerization reactor 135a are contemplated. Thus, oligomerizing ethanol in oligomerization unit 135 can include dehydrating ethanol to form ethylene; oligomerizing ethylene to form a $C_3$ to $C_8$ olefin; and oligomerizing the $C_3$ to $C_8$ olefin to form the second hydrocarbon stream 117.

The product made in the first oligomerization reactor 135a—e.g., the $C_3$-$C_8$ olefin(s)—is then fed to a second oligomerization reactor 135b where the olefins undergo a second oligomerization operation to form the hydrocarbon(s) 117b. Catalysts useful for the second oligomerization operation include Lewis acid catalysts, such as aluminum trichloride ($AlCl_3$) or boron trifluoride (BF3) solid Lewis acid catalysts such as synthetic or natural zeolites, acid clays, polymeric acidic resins, amorphous solid catalysts such as silica-alumina, and heteropoly acids such as the tungsten zirconates, tungsten molybdates, tungsten vanadates, phosphotungstates and molybdotungstovanadogermanates; and ion-exchange resins such as Amberlyst. The operating temperature of the second oligomerization reactor 135b can be less than about 450° C., such as from about 50° C. to about 400° C., such as from about 100° C. to about 350° C., such as from about 200° C. to about 300° C. The second oligomerization reactor 135b can be set to a pressure from about 10 psig to about 1500 psig, such as from about 25 psig to about 1000 psig, such as from about 50 psig to about 750 psig, such as from about 100 psig to about 500 psig. Other operating parameters of the second oligomerization reactor 135b are contemplated. The product of the first oligomerization reactor 135a can be fed to the second oligomerization reactor 135b with a WHSV value that is from about 0.05 h$^{-1}$ to about 200 h$^{-1}$, such as from about 0.1 h$^{-1}$ to about 150 h$^{-1}$, such as from about 0.2 h$^{-1}$ to about 100 h$^{-1}$, such as from about 0.5 h$^{-1}$ to about 50 h$^{-1}$, such as from about 1 h$^{-1}$ to about 10 h$^{-1}$, though other values are contemplated. The hydrocarbon(s) 117b formed from the second oligomerization process can include various hydrocarbons, such as those hydrocarbons having a carbon number from about $C_4$ to about $C_{25}$, such as from about $C_6$ to about $C_{24}$, such as from about $C_8$ to about $C_{23}$, such as from about $C_{11}$ to about $C_{23}$. These hydrocarbons can be linear or branched olefins with low concentrations of aromatic compounds.

Additionally, or alternatively, the ethanol feedstock or ethanol-containing feedstock produced by fermentation can be subjected to a one-operation dehydration-oligomerization process where the ethanol is converted to hydrocarbon(s)

117b having a carbon number from about $C_2$ to about $C_{12}$, such as from about $C_3$ to about $C_8$. Here, and in some aspects, the dehydration unit 133 and the oligomerization unit 135 may not be used as separate units, but instead the ethanol conversion unit 134 may be used by adapting the units with known methods and catalysts. Useful catalysts include zeolites such as β-type zeolites, MFI framework zeolites (e.g., ZSM-5), FAU-type zeolites, MCM-type and/or Y-type zeolites. Such catalysts enable dehydration of ethanol to olefin(s) with subsequent oligomerization of the olefin(s). The one-operation oligomerization process can be performed in any suitable reactor.

The operating temperature of the reactor(s) used for the one-operation dehydration-oligomerization process can be performed at about 250° C. or more, such as from about 275° C. to about 550° C., such as from about 300° C. to about 500° C., such as from about 350° C. to about 450° C., such as from about 375° C. to about 425° C. The dehydration-oligomerization process can be performed at a pressure from about 0 psig to about 1500 psig, such as from about 5 psig to about 1200 psig, such as from about 10 psig to about 1,000 psig, such as from about 50 psig to about 750 psig, such as from about 100 psig to about 500 psig. Other operating parameters of the reactors used for the one-operation dehydration-oligomerization process are contemplated.

Another process of forming a fuel composition can include one or more of the following operations:

(a) converting biomass to a terpene stream and a dried carbon-containing material;

(b) introducing the terpene stream with hydrogen and a hydrotreatment catalyst to form a first hydrocarbon stream;

(c) introducing the dried carbon-containing material with a gasification agent to form syngas;

(d) converting at least a portion of the syngas to a second hydrocarbon stream comprising: introducing the syngas to a Fischer-Tropsch catalyst to form a second hydrocarbon stream, or introducing the syngas to a microorganism to form ethanol and oligomerizing ethanol to form a second hydrocarbon stream; and (e) introducing the first hydrocarbon stream to the second hydrocarbon stream to form a fuel composition.

These operations are described above with respect to FIG. 2.

One or more products from the Fischer-Tropsch process (e.g., the hydrocarbon(s) 117a), the two-operation oligomerization process (e.g., the hydrocarbon(s) 117b), and/or the one-operation oligomerization process of operation 240 (also, e.g., the hydrocarbon(s) 117b) can be combined to form the second hydrocarbon stream 117. The second hydrocarbon stream 117, can include e.g., jet fuel, diesel fuel, gasoline, naphtha, or combinations thereof, such as jet fuel, diesel fuel, or combinations thereof.

The composition of the first hydrocarbon stream 109 and the second hydrocarbon stream 117 can be the same or different. The amount of jet fuel in the first hydrocarbon stream 109 can be from about 0 wt % to about 100 wt %, such as from about 1 wt % to about 99 wt %, such as from about 5 wt % to about 95 wt %, such as from about 10 wt % to about 90 wt %, such as from about 20 wt % to about 80 wt %, such as from about 30 wt % to about 70 wt %, such as from about 40 wt % to about 60 wt %, such as from about 45 wt % to about 55 wt %, based on the total weight of the first hydrocarbon stream 109. In some aspects, the amount of jet fuel in the first hydrocarbon stream 109 is less than about 50 wt %, such as from about 0 wt % to about 50 wt %, such as from about 1 wt % to about 45 wt %, such as from about 10 wt % to about 40 wt %, such as from about 20 wt % to about 30 wt %, based on the total weight of the first hydrocarbon stream 109.

Additionally, or alternatively, and in some aspects, an amount of diesel fuel in the first hydrocarbon stream 109 is from about 0 wt % to about 100 wt %, such as from about 1 wt % to about 99 wt %, such as from about 5 wt % to about 95 wt %, such as from about 10 wt % to about 90 wt %, such as from about 20 wt % to about 80 wt %, such as from about 30 wt % to about 70 wt %, such as from about 40 wt % to about 60 wt %, such as from about 45 wt % to about 55 wt %, based on the total weight of the first hydrocarbon stream 109. In some aspects, the amount of diesel fuel in the first hydrocarbon stream 109 is less than about 50 wt %, such as from about 0 wt % to about 50 wt %, such as from about 1 wt % to about 45 wt %, such as from about 10 wt % to about 40 wt %, such as from about 20 wt % to about 30 wt %, based on the total weight of the first hydrocarbon stream 109.

Process 200 further includes introducing, at operation 250, the first hydrocarbon stream 109 flowing out of the hydrotreatment unit 107 to the second hydrocarbon stream 117 flowing out of the syngas conversion unit 115 to form a fuel composition 120. The first hydrocarbon stream 109 and the second hydrocarbon stream 117 can be combined in collection unit 119, which can be a storage tank, a pipeline, a tank truck, a rail car, or another suitable means to store and/or transport the fuel composition. The fuel composition 120 includes jet fuel, diesel fuel, gasoline, naphtha, or a combination thereof, in any suitable proportion.

An amount of jet fuel in the fuel composition 120 can be from about 0 wt % to about 100 wt %, such as from about 1 wt % to about 99 wt %, such as from about 5 wt % to about 95 wt %, such as from about 10 wt % to about 90 wt %, such as from about 20 wt % to about 80 wt %, such as from about 30 wt % to about 70 wt %, such as from about 40 wt % to about 60 wt %, such as from about 45 wt % to about 55 wt %, based on the total weight of the fuel composition 120. In some aspects, the amount of jet fuel in the fuel composition 120 is less than about 50 wt %, such as from about 0 wt % to about 50 wt %, such as from about 1 wt % to about 45 wt %, such as from about 10 wt % to about 40 wt %, such as from about 20 wt % to about 30 wt %, based on the total weight of the fuel composition 120.

Additionally, or alternatively, and in some aspects, an amount of diesel fuel in the fuel composition 120 is from about 0 wt % to about 100 wt %, such as from about 1 wt % to about 99 wt %, such as from about 5 wt % to about 95 wt %, such as from about 10 wt % to about 90 wt %, such as from about 20 wt % to about 80 wt %, such as from about 30 wt % to about 70 wt %, such as from about 40 wt % to about 60 wt %, such as from about 45 wt % to about 55 wt %, based on the total weight of the fuel composition 120. In some aspects, the amount of diesel fuel in the fuel composition 120 is less than about 50 wt %, such as from about 0 wt % to about 50 wt %, such as from about 1 wt % to about 45 wt %, such as from about 10 wt % to about 40 wt %, such as from about 20 wt % to about 30 wt %, based on the total weight of the fuel composition 120.

The fuel composition 120 has increased energy density relative to petroleum-derived fuels as a result of, e.g., the composition of the first hydrocarbon stream 109 containing, e.g., pinanes and derivatives thereof, the composition of the second hydrocarbon stream 117, e.g., Fischer-Tropsch fuels, and the combination of these streams. Upon combustion, the streams (individually or combined) release higher amounts of energy relative to petroleum-derived fuels.

The present disclosure provides, among others, the following examples, each of which can be considered as optionally including any alternate aspects:

Clause 1. A process, comprising:

drying a carbon-containing feedstock comprising biomass to form a terpene stream and a dried carbon-containing material;

hydrotreating the terpene stream to form a first hydrocarbon stream;

gasifying the dried carbon-containing material to form a syngas;

converting the syngas to a second hydrocarbon stream; and introducing the first hydrocarbon stream and the second hydrocarbon stream to form a fuel composition.

Clause 2. The process of Clause 1, wherein the converting the syngas to a second hydrocarbon stream comprises:

introducing the syngas to a Fischer-Tropsch catalyst; or introducing the syngas to a microorganism.

Clause 3. The process of claim 2, wherein when the process comprises introducing the syngas to the microorganism, the microorganism comprises *Moorella, Clostridium* (e.g., *Clostridium autoethanogenum*), *Ruminococcus, Acetobacterium, Eubacterium, Butyribacterium, Oxobacter, Methanosarcina, Methanosarcina*, and *Desulfotomaculum*, or combinations thereof.

Clause 4. The process of any one of Clauses 1-3, wherein:

the syngas comprises $H_2$ and CO; and the syngas has a molar ratio of $H_2$:CO from about 1.8:1 to about 2.1:1.

Clause 5. The process of any one of Clauses 1-4, wherein the first hydrocarbon stream comprises diesel fuel, jet fuel, or a combination thereof.

Clause 6. The process of any one of Clauses 1-5, wherein the second hydrocarbon stream comprises diesel fuel, jet fuel, or a combination thereof.

Clause 7. The process of any one of Clauses 1-6, wherein the first hydrocarbon stream is different from the second hydrocarbon stream.

Clause 8. The process of any one of Clauses 1-7, wherein hydrogen for hydrotreating the terpene stream is formed by electrolysis, steam-methane reforming, gasification, or combinations thereof.

Clause 9. The process of any one of Clauses 1-8, wherein the terpene stream comprises an amount of α-pinene and β-pinene of about 50 wt % or more.

Clause 10. A process, comprising:

converting biomass to a terpene stream and a dried carbon-containing material;

introducing the terpene stream with hydrogen and a hydrotreatment catalyst to form a first hydrocarbon stream;

introducing the dried carbon-containing material with a gasification agent to form a syngas;

converting at least a portion of the syngas to a second hydrocarbon stream comprising:

introducing the syngas to a Fischer-Tropsch catalyst to form the second hydrocarbon stream; or introducing the syngas to a microorganism to form ethanol and oligomerizing ethanol to form the second hydrocarbon stream; and introducing the first hydrocarbon stream to the second hydrocarbon stream to form a fuel composition.

Clause 11. The process of Clause 10, wherein when the process comprises introducing the syngas to the microorganism to form ethanol and oligomerizing ethanol to form the second hydrocarbon stream, the microorganism comprises *Moorella, Clostridium* (e.g., *Clostridium autoethanogenum*), *Ruminococcus, Acetobacterium, Eubacterium, Butyribacterium, Oxobacter, Methanosarcina, Methanosarcina*, and *Desulfotomaculum*, or combinations thereof.

Clause 12. The process of Clause 11, wherein the oligomerizing ethanol comprises:

dehydrating ethanol to form ethylene;

oligomerizing ethylene to form a $C_3$ to $C_8$ olefin; and oligomerizing the $C_3$ to $C_8$ olefin to form the second hydrocarbon stream.

Clause 13. The process of Clause 11, wherein the oligomerizing ethanol comprises introducing ethanol to a zeolite to form the second hydrocarbon stream, the second hydrocarbon stream comprising a $C_2$-$C_{12}$ olefin.

Clause 13. The process of Clause 11, wherein the oligomerizing ethanol comprises introducing ethanol to a zeolite to form the second hydrocarbon stream, the second hydrocarbon stream comprising a $C_2$-$C_{12}$ olefin.

Clause 14. The process of any one of Clauses 10-13, wherein the syngas comprises $H_2$ and CO, and the syngas has a molar ratio of $H_2$:CO from about 1.8:1 to about 2.1:1.

Clause 15. The process of any one of Clauses 10-14, wherein the first hydrocarbon stream comprises diesel fuel, jet fuel, or a combination thereof.

Clause 16. The process of any one of Clauses 10-15, wherein the second hydrocarbon stream comprises diesel fuel, jet fuel, or a combination thereof.

Clause 17. An apparatus, comprising:

a drying unit coupled at a first end with a first end of a gasification unit, the drying unit further coupled at a second end with a first end of a hydrotreatment unit;

a drying unit coupled at a first end with a first end of a gasification unit, the drying unit further coupled at a second end with a first end of a hydrotreatment unit;

a syngas conversion unit coupled at a first end with a second end of the gasification unit; and a collection unit coupled at a first end with a second end of the hydrotreatment unit, the collection unit further coupled at a second end with a second end of the syngas conversion unit Clause 18. The apparatus of Clause 17, wherein:

the drying unit is configured to convert a carbon-containing feedstock comprising forest residues to a dried carbon-containing material;

the gasification unit is configured to convert the dried carbon-containing material to a conversion product comprising $H_2$ and CO; and the syngas conversion unit comprises:

a Fischer-Tropsch unit; or a fermentation unit coupled to an ethanol conversion unit.

Clause 19. The apparatus of Clause 17 or 18, wherein a hydrotreatment catalyst in the hydrotreatment unit converts pinene in a terpene stream to pinane.

Clause 20. The apparatus of any one of Clauses 17-19, further comprising an electrolysis unit coupled at a first end to a third end of the hydrotreatment unit.

Aspects described herein enable formation of fuel compositions at low costs and high volumes from, e.g., biomass. Examples described herein enable, e.g., reduced manufacturing costs due to, e.g., joining the process for producing the first hydrocarbon stream 109 (e.g., hydrotreatment) and the process for producing second hydrocarbon stream 117 (e.g., gasification and Fischer-Tropsch reaction) into a single, integrated process. Having a single, integrated process increases the volumes of fuels produced relative to other processes, thereby lowering fuel production costs.

All documents described herein are incorporated by reference herein, including any priority documents and/or testing procedures to the extent they are not inconsistent with this text. Further, all documents and references cited herein, including testing procedures, publications, patents, journal articles, etc. are herein fully incorporated by reference for all jurisdictions in which such incorporation is permitted and to the extent such disclosure is consistent with the description of the present disclosure. As is apparent from the foregoing general description and the specific aspects, while forms of the aspects have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa, e.g., the terms "comprising," "consisting essentially of," "consisting of" also include the product of the combinations of elements listed after the term.

As used herein, a "composition" can include component(s) of the composition and/or reaction product(s) of two or more components of the composition. Compositions can include reaction intermediates.

As used herein, the indefinite article "a" or "an" shall mean "at least one" unless specified to the contrary or the context clearly indicates otherwise. For example, aspects comprising "a metal chalcogenide" include aspects comprising one, two, or more metal chalcogenides, unless specified to the contrary or the context clearly indicates only one metal chalcogenide is included.

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

What is claimed is:

1. A process, comprising:
   drying a carbon-containing feedstock comprising biomass to form a terpene stream and a dried carbon-containing material using an integrated apparatus comprising a drying unit coupled to a gasification unit and coupled to a hydrotreatment unit, wherein the drying unit is coupled to the gasification unit via a first material transfer line and to the hydrotreatment unit via a second material transfer line, and wherein the dried carbon-containing material is directly transferred from the drying unit to the gasification unit through the first material transfer line;
   hydrotreating the terpene stream to form a first hydrocarbon stream;
   gasifying the dried carbon-containing material to form a syngas;
   converting the syngas to a second hydrocarbon stream; and
   combining the first hydrocarbon stream and the second hydrocarbon stream in a collection unit coupled to both the hydrotreatment unit and a syngas conversion unit to form a fuel composition, wherein the collection unit comprises a first inlet line receiving the first hydrocarbon stream from the hydrotreatment unit and a second inlet line receiving the second hydrocarbon stream from the syngas conversion unit, and wherein the collection unit is configured to blend the first and second hydrocarbon streams.

2. The process of claim 1, wherein the converting the syngas to a second hydrocarbon stream in the syngas conversion unit comprises:
   introducing the syngas to a Fischer-Tropsch catalyst; or
   introducing the syngas to a microorganism.

3. The process of claim 2, wherein the microorganism comprises *Moorella, Clostridium* including *Clostridium autoethanogenum, Ruminococcus, Acetobacterium, Eubacterium, Butyribacterium, Oxobacter, Methanosarcina, Desulfotomaculum*, or combinations thereof.

4. The process of claim 1, wherein:
   the syngas comprises $H_2$ and CO; and
   the syngas has a molar ratio of $H_2$:CO from about 1.8:1 to about 2.1:1.

5. The process of claim 1, wherein the first hydrocarbon stream comprises diesel fuel, jet fuel, or a combination thereof.

6. The process of claim 1, wherein the second hydrocarbon stream comprises diesel fuel, jet fuel, or a combination thereof.

7. The process of claim 1, wherein the first hydrocarbon stream is different from the second hydrocarbon stream.

8. The process of claim 1, wherein hydrogen for hydrotreating the terpene stream is formed by electrolysis, steam-methane reforming, gasification, or combinations thereof.

9. The process of claim 1, wherein the terpene stream comprises an amount of α-pinene and β-pinene of about 50 wt % or more.

10. A process, comprising:
   converting biomass to a terpene stream and a dried carbon-containing material using an integrated apparatus comprising a coupling between processing units;
   introducing the terpene stream with hydrogen and a hydrotreatment catalyst to form a first hydrocarbon stream;
   introducing the dried carbon-containing material with a gasification agent to form a syngas, wherein the dried carbon-containing material is transferred from a drying unit to a gasification unit through a material transfer line;

converting at least a portion of the syngas to a second hydrocarbon stream comprising:

introducing the syngas to a Fischer-Tropsch catalyst to form the second hydrocarbon stream; or introducing the syngas to a microorganism to form ethanol and oligomerizing ethanol to form the second hydrocarbon stream; and combining the first hydrocarbon stream to the second hydrocarbon stream in a shared collection unit to form a fuel composition, wherein the shared collection unit is positioned to receive streams from multiple processing units via separate inlet lines and is configured to blend the streams.

11. The process of claim 10, wherein when the process comprises introducing the syngas to a microorganism to form ethanol and oligomerizing ethanol to form the second hydrocarbon stream, the microorganism comprises *Moorella, Clostridium* including *Clostridium autoethanogenum, Ruminococcus, Acetobacterium, Eubacterium, Butyribacterium, Oxobacter, Methanosarcina, Methanosarcina, Desulfotomaculum*, or combinations thereof.

12. The process of claim 11, wherein the oligomerizing ethanol comprises:

dehydrating ethanol to form ethylene;

oligomerizing the ethylene to form a $C_3$ to $C_8$ olefin; and oligomerizing the $C_3$ to $C_8$ olefin to form the second hydrocarbon stream.

13. The process of claim 11, wherein the oligomerizing ethanol comprises introducing ethanol to a zeolite to form the second hydrocarbon stream, the second hydrocarbon stream comprising a $C_2$-$C_{12}$ olefin.

14. The process of claim 10, wherein the syngas comprises $H_2$ and CO, and the syngas has a molar ratio of $H_2$:CO from about 1.8:1 to about 2.1:1.

15. The process of claim 10, wherein the first hydrocarbon stream comprises diesel fuel, jet fuel, or a combination thereof.

16. The process of claim 10, wherein the second hydrocarbon stream comprises diesel fuel, jet fuel, or a combination thereof.

* * * * *